(12) United States Patent
Franke et al.

(10) Patent No.: US 9,845,276 B2
(45) Date of Patent: Dec. 19, 2017

(54) PRODUCTION OF N-PENTANAL FROM LOW-BUTENE FEEDSTOCK MIXTURES

(71) Applicant: Evonik Degussa GmbH, Essen (DE)

(72) Inventors: Robert Franke, Marl (DE); Lena Altmann, Dorsten (DE); Corinna Hecht, Haltern am See (DE); Benedikt Dercks, Bochum (DE); Hanna Spohr, Duisburg-Baerl (DE); Horst-Werner Zanthoff, Mülheim a.d. Ruhr (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/491,173

(22) Filed: Apr. 19, 2017

(65) Prior Publication Data

US 2017/0334822 A1  Nov. 23, 2017

(30) Foreign Application Priority Data

May 19, 2016  (EP) .................................... 16170274

(51) Int. Cl.
*C07C 45/50* (2006.01)
*C07C 5/333* (2006.01)
*C07C 5/03* (2006.01)
*B01J 19/24* (2006.01)

(52) U.S. Cl.
CPC ........... *C07C 45/505* (2013.01); *B01J 19/245* (2013.01); *B01J 19/2445* (2013.01); *C07C 5/03* (2013.01); *C07C 5/333* (2013.01); *B01J 2219/00132* (2013.01); *B01J 2219/24* (2013.01); *C07C 2521/04* (2013.01); *C07C 2523/62* (2013.01)

(58) Field of Classification Search
CPC .......... C07C 45/505; C07C 5/05; C07C 5/333
USPC ....................................................... 568/451
See application file for complete search history.

(56) References Cited

U.S. PATENT DOCUMENTS

| | | |
|---|---|---|
| 3,665,049 A | 5/1972 | Cornelius et al. |
| 3,778,388 A | 12/1973 | Cornelius et al. |
| 4,152,365 A | 5/1979 | Drehman |
| 4,926,005 A | 5/1990 | Olbrich et al. |
| 5,151,401 A | 9/1992 | Schubert et al. |
| 5,998,685 A * | 12/1999 | Nierlich ................ C07C 11/02 568/909 |
| 6,914,162 B2 | 7/2005 | Richter et al. |
| 7,714,179 B2 * | 5/2010 | Sigl ......................... C07C 6/04 568/429 |
| 8,581,008 B2 | 11/2013 | Kaizik et al. |
| 8,841,481 B2 | 9/2014 | Zanthoff et al. |
| 8,889,935 B2 | 11/2014 | Maschmeyer |
| 9,272,973 B2 | 3/2016 | Fridag et al. |
| 2006/0122436 A1 | 6/2006 | Schindler et al. |
| 2016/0236150 A1 | 8/2016 | Geilen et al. |
| 2016/0257634 A1 | 9/2016 | Dyballa et al. |
| 2016/0304426 A1 | 10/2016 | Becker et al. |
| 2016/0326197 A1 | 11/2016 | Dyballa et al. |

FOREIGN PATENT DOCUMENTS

| | | |
|---|---|---|
| MY | 140652 A | 1/2010 |
| WO | 2004041763 A1 | 5/2004 |
| WO | 2014192020 A1 | 12/2014 |
| WO | 2015086634 A1 | 6/2015 |
| WO | 2015132068 A1 | 9/2015 |

OTHER PUBLICATIONS

European Search Report dated Nov. 21, 2016 in EP 16170274.1 (8 pages).

* cited by examiner

*Primary Examiner* — Sikarl Witherspoon
(74) *Attorney, Agent, or Firm* — Philip P. McCann; Smith Moore Leatherwood LLP

(57) ABSTRACT

The invention is concerned with the issue of how to produce n-pentanal by hydroformylation from feedstock mixtures comprising a small proportion of n-butene and a large proportion of n-butane. Specifically, solutions for further optimizing established processes for hydroformylation of such low-butene mixtures in terms of material utilization are sought. The present invention has for its object to enhance the material utilization of the feedstock mixture in the production of n-pentanal from feedstock mixtures having a small proportion of n-butene and a large proportion of n-butane. The process shall be capable of economic operation on an industrial scale. In particular an existing oxo plant shall be honed to achieve better raw material utilization. This object is achieved by a combination of a hydroformylation and a dehydrogenation, wherein said combination has the special feature that the dehydrogenation is arranged after the hydroformylation in the downstream direction and is thus markedly smaller than conventional dehydrogenations provided upstream. A skillful product removal effectively removes contaminants formed in the process.

20 Claims, 3 Drawing Sheets

PRODUCTION OF N-PENTANAL FROM LOW-BUTENE FEEDSTOCK MIXTURES

This application claims the benefit of European Application No. 16170274.1 filed on May 19, 2016, the disclosure of which is expressly incorporated herein by reference.

BACKGROUND

The invention is concerned with the issue of how to produce n-pentanal by hydroformylation from feedstock mixtures comprising a small proportion of n-butene and a large proportion of n-butane. Specifically, solutions for further optimizing established processes for hydroformylation of such low-butene mixtures in terms of material utilization are sought.

The substance groups discussed in this connection are essentially alkenes (olefins), alkanes (paraffins), aldehydes and alcohols. These terms are used here in accordance with the terminology customary in chemistry.

In organic chemistry, substance groups are generally classified and named by the number of carbon atoms therein. The substance class of interest is preceded by the prefix $C_n$, where n is the number of respective carbon atoms present in the substance. When reference is made to $C_4$ alkenes for example, this is understood to mean the four isomeric olefins having four carbon atoms, namely isobutene, 1-butene, cis-2-butene and trans-2-butene.

The saturated alkanes have barely any reactivity and are therefore used predominantly as fuel or aerosol propellant.

Meanwhile, it is possible to use the more reactive alkenes to form hydrocarbons having a greater number of carbon atoms which open up a broad spectrum of application and hence achieve higher sale prices than the starting materials having a smaller number of carbon atoms. This is how industrial organic chemistry adds value.

An economically important substance class which is produced from lower alkenes for this reason is that of the aldehydes. The aldehyde having three carbon atoms is called propanal. Two $C_4$-aldehydes exist, namely n-butanal and isobutanal.

The aldehydes having five carbon atoms include the isomeric substances n-pentanal (also known as valeraldehyde), isopentanal (isovaleraldehyde), (S)-2-methylbutyraldehyde, (R)-2-methylbutyraldehyde and tert-pentanal. Valeraldehyde, used as a vulcanization accelerator, is of economic importance. Valeraldehyde may also be converted by aldol condensation and subsequent hydrogenation into 2-propylheptanol, an alcohol which is in turn a starting material for further syntheses toward PVC plasticizers, detergents and lubricants. Details may be found in U.S. Pat. No. 8,581,008.

n-Pentanal is produced by hydroformylation of n-butene.

n-Butene is an umbrella term for the three linear $C_4$-olefins 1-butene, cis-2-butene and trans-2-butene. A mixture comprising these three isomeric substances is normally at issue; the precise composition depends on the thermodynamic state.

Hydroformylation (the oxo process) is generally understood to mean the conversion of unsaturated compounds such as in particular olefins with synthesis gas (hydrogen and carbon monoxide) into aldehydes having a number of carbon atoms one higher than the number of carbon atoms in the starting compounds. $C_5$ aldehydes are accordingly produced by hydroformylating butene.

A comprehensive account of the current state of the art of hydroformylation may be found in:

Armin Börner, Robert Franke: Hydroformylation. Fundamentals, Processes and Applications in Organic Synthesis. Volumes 1 and 2. Wiley-VCH, Weinheim, Germany 2016.

An established process for producing n-pentanal is disclosed in U.S. Pat. No. 9,272,973. The inventors proceed from this closest prior art.

In the hydroformylation for producing valeraldehyde practiced there an input mixture containing 35% 2-butenes and only 1% 1-butene is used. The remainder is butane which is inert toward the hydroformylation. The mixture extremely low in 1-butene is hydroformylated in the presence of a homogeneous catalyst system comprising a particular symmetrical biphosphite ligand which is stabilized by addition of an amine. Isononyl benzoate is mentioned as a solvent. With this catalyst system, butene conversions of 60% to 75% are achieved.

To enhance material efficiency WO2015/086634A1 proposes removing the unconverted alkenes from the reaction mixture using a membrane and converting them in a second hydroformylation stage with the aid of SILP technology. The inert alkanes are likewise discharged from the process with the membrane and thus do not cause any further disruption in the hydroformylation. This measure allows for very good material utilization, i.e. conversion into aldehydes, of the butenes present in the feedstock mixture. However, the butanes present in the feedstock mixture remain unutilized.

One option for better chemical utilization of alkanes than incinerating them is to dehydrogenate them. Dehydrogenation allows alkanes to be converted into more reactive and thus chemically versatile alkenes. Naturally, this requires energy. Since alkanes are relatively cheap raw materials a cost-effective dehydrogenation, especially performed in energy-efficient fashion, achieves significant added value. There is therefore a considerable range of commercially available technologies for dehydrogenation of alkanes, more particularly the $C_3$-alkane propane, on offer. A comprehensive market analysis may be found in:

Victor Wan, Marianna Asaro: Propane Dehydrogenation Process Technologies, October 2015. Obtainable from IHS CHEMICAL, Process Economics Program RP267A.

Since propane dehydrogenation is operated in the sphere of naphtha crackers these processes are all configured and optimized for a petrochemical-scale throughput. Thus the capacity of a propane dehydrogenation according to the UHDE STAR® process is approximately 500 000 t/a of propylene (see PEP-Report cited above, pages 2-11). These are scales which differ very markedly from those of industrially operated hydroformylation; thus the capacity of a large oxo plant is only 100 000 t/a (Börner/Franke, Introduction). It thus hardly makes economic sense to dehydrogenate propane with the aid of a costly large-scale plant and then to hydroformylate a small portion of the recovered propene unless the excess propene is used for instance for production of polypropylene.

It is apparently for this reason that literature reports of a combination of a dehydrogenation with a subsequent hydroformylation are conspicuous in their rarity:

In the field of $C_3$-chemistry, U.S. Pat. No. 6,914,162B2 describes a combination of a propane dehydrogenation with subsequent hydroformylation of the obtained propene. The dehydrogenation is arranged before the hydroformylation in the upstream direction. In this connection "upstream" means further up the added-value chain. A similar process which also operates with n-butane as the feedstock is outlined in US2006/0122436A1.

WO2015/132068A1 likewise describes the dehydrogenation of $C_3$ to $C_5$ alkanes with downstream (i.e. in the direction of added value) hydroformylation. However, the latter is carried out in the presence of a heterogeneous catalyst system which is why this process differs markedly from the presently industrially operated, homogeneously catalyzed oxo processes in terms of apparatus.

Another reason why the dehydrogenation and the hydroformylation are not combined in practice is that the dehydrogenation affords not only the desired alkenes but also very many other hydrocarbons which are a great hindrance in the hydroformylation. One example thereof is 1,3-butadiene for instance which acts as an inhibitor in the hydroformylation. Such contaminants must first be removed from the alkenes at great inconvenience (i.e. cost) before said alkenes may be hydroformylated.

The intermediate removal of substances formed in the dehydrogenation and undesired in the hydroformylation is addressed in U.S. Pat. No. 8,889,935. However this process is used primarily to produce the linear $C_4$-olefin 1-butene by dehydrogenation of n-butane. It is proposed in this connection that the 2-butene generated as a byproduct in the dehydrogenation of n-butane be converted into n-pentanal by hydroformylation. Contaminants formed in the dehydrogenation such as 1,3-butadiene are derivatized/selectively hydrogenated before hydroformylation.

U.S. Pat. No. 5,998,685 discloses a process where feedstock mixtures comprising n-butane and isobutane are dehydrogenated and the thus obtained alkenes are initially oligomerized and the obtained olefin oligomers are finally hydroformylated. Since the catalysts employed in the oligomerization are likewise very sensitive to byproducts generated in the butane dehydrogenation a costly and complex purification is interposed.

In terms of the prior art it can be said that due to the differences in throughput rates and the inevitably formed contaminants the alkane dehydrogenation with subsequent hydroformylation has acquired no practical significance.

However, the reverse combination, where the hydroformylation is arranged in front of the dehydrogenation in the upstream direction, is hardly found in the patent literature either:

Thus MY140652A discloses a process for producing oxo alcohols where the alkanes not converted in the hydroformylation are removed from the hydroformylation mixture and subjected to a dehydrogenation. The thus obtained alkenes are mixed with the fresh feedstock and also isomerized before hydroformylation. The feedstock originates from a Fischer-Tropsch process and essentially comprises alkanes and alkenes having 8 to 10 carbon atoms.

In this process the alkanes are removed by distillation from alkenes not converted in the hydroformylation at great cost and complexity before dehydrogenation. This is because the presence of alkenes in the dehydrogenation is undesirable since due to their up to four-fold higher reactivity compared to alkanes they form many oxidation products such as CO and $CO_2$ which ultimately leads to rapid coking of the catalysts: cf. R. Nielsen: Process Economics Program Report 35F On-Purpose Butadiene Production II. December 2014, page 39 available from ihs.com/chemical. For the same reason providers of commercial dehydrogenation processes advise against introducing alkenes into the dehydrogenation.

The practical problem of contaminants requiring complex and costly removal is thus also present when a dehydrogenation is arranged downstream of a hydroformylation. In addition, even a world-scale oxo plant would scarcely be capable of keeping a dehydrogenation plant on a customary scale operating at anything approaching full capacity.

In conclusion it may be noted that the combination of dehydrogenation and hydroformylation or of hydroformylation and dehydrogenation is not industrially operated since the industrial scales do not coincide and because the specifications of the products and reactants of the respective processes are incompatible and thus necessitate a costly intermediate removal.

SUMMARY

Against this background, the present invention has for its object the development of a process for producing n-pentanal from feedstock mixtures comprising a small proportion of n-butene and a large proportion of n-butane in such a way that the material utilization of the feedstock mixture is enhanced. The process shall be capable of economic operation on an industrial scale. In particular an existing oxo plant shall be honed to achieve better raw material utilization.

This object is achieved by a combination of a hydroformylation and a dehydrogenation, wherein said combination has the special feature that the dehydrogenation is arranged after the hydroformylation in the downstream direction and is thus markedly smaller than conventional dehydrogenations provided upstream. A skillful product removal effectively removes contaminants formed in the process.

BRIEF DESCRIPTION OF THE DRAWINGS

Reference will now be made to the accompanying drawings wherein like reference characters designate the same or similar parts throughout the several views, and wherein.

DETAILED DESCRIPTION

Figure 1:
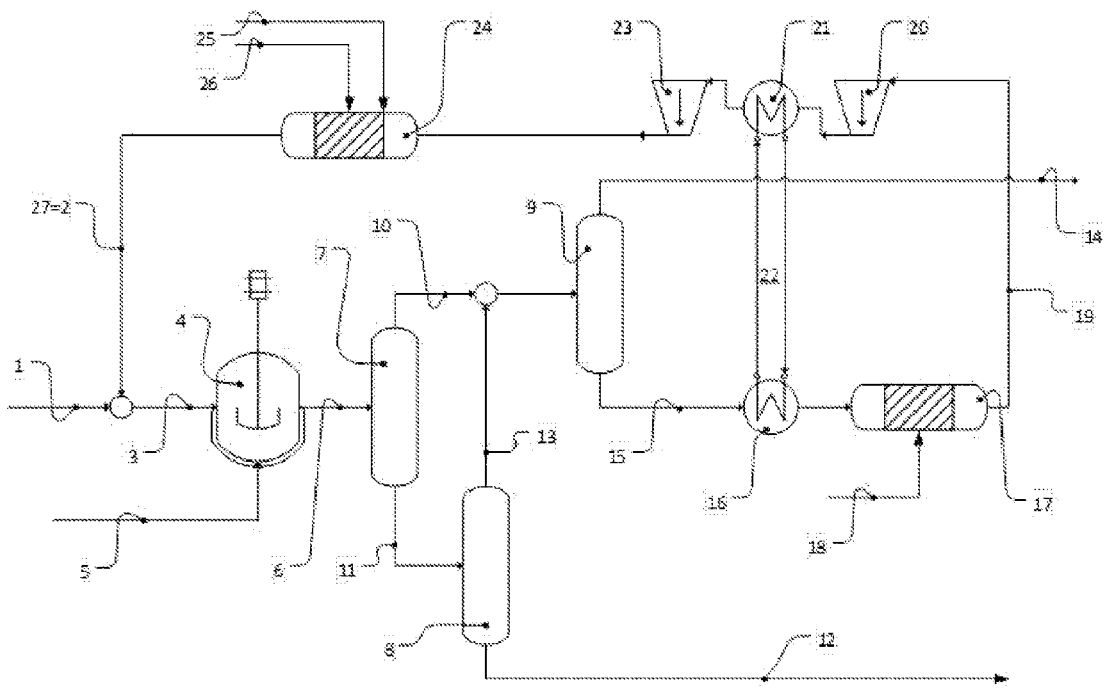
FIG. 1 is a process flow diagram of the basic concept.

Specifically, the invention provides a process for producing n-pentanal comprising the steps of:
a) providing a feedstock mixture having the following composition which sums to 100 wt %:
   n-butane: 70 wt % to 90 wt %;
   n-butene: 10 wt % to 30 wt %;
   1-butene: 0 wt % to 3 wt %;
   isobutene: 0 wt % to 3 wt %;
   isobutane: 0 wt % to 3 wt %;
   1,3-butadiene: 0 wt % to 1 wt %;
   other substances: 0 wt % to 1 wt %;
b) mixing the feedstock mixture with a recyclate to obtain a feed;
c) treating the feed with carbon monoxide and hydrogen in the presence of a first catalyst system to convert at least a portion of the n-butene present in the feed into aldehydes by hydroformylation to obtain a hydroformylation mixture;
d) recovering a primary product fraction from the hydroformylation mixture, wherein the primary product fraction has the following composition which sums to 100 wt %:

n-pentanal: 90 wt % to 98.5 wt %;
2-methylbutanal: 0 wt % to 5 wt %;
3-methylbutanal: 0 wt % to 3 wt %;
other substances: 0 wt % to 2 wt %;
e) recovering a subsidiary fraction from the hydroformylation mixture, wherein the subsidiary fraction has the following composition which sums to 100 wt %:
n-butane: 80 wt % to 92 wt %;
n-butene: 8 wt % to 20 wt %;
other substances: 0 wt % to 1 wt %;
f) subjecting the subsidiary fraction to a dehydrogenation in the presence of a second catalyst system to obtain a dehydrogenation mixture having the following composition which sums to 100 wt %:
n-butene: 50 wt % to 60 wt %;
n-butane: 40 wt % to 50 wt %;
methane: 0 wt % to 4 wt %;
ethene: 0 wt % to 3 wt %;
propene: 0 wt % to 2 wt %;
1,3-butadiene: 0 wt % to 3 wt %;
other substances: 0 wt % to 1 wt %;
g) subjecting the dehydrogenation mixture to a selective hydrogenation in the presence of a third catalyst system to obtain a hydrogenation mixture having the following composition which sums to 100 wt %:
n-butene: 50 wt % to 60 wt %;
n-butane: 40 wt % to 50 wt %;
1,3-butadiene: 0 ppm by weight to 500 ppm by weight;
other substances: 0 wt % to 5 wt %;
h) direct use of the hydrogenation mixture as recyclate or
purification of the hydrogenation mixture to obtain the recyclate.

The invention is based on the realization that it is possible at unexpectedly low cost and complexity to recover the n-butane not convertible in the hydroformylation as a subsidiary fraction, to dehydrogenate it, and to recycle the thus obtained butenes back into the hydroformylation to convert them into the desired aldehydes there. The carbon atoms present in the feedstock mixture are thus utilized very efficiently. It is surprising that the byproducts generated in not insignificant amounts in the dehydrogenation (these generally make up about 8 wt % of the effluent from the dehydrogenation) can be removed with separating means which are in any case present and this is why the additional cost and complexity for contaminant removal is low. This is because the hydroformylation is sensitive only to a few byproducts formed in a downstream dehydrogenation and, in addition to the n-pentanol, can even form further products of value from some of them. This has the result that the process is economic notwithstanding that the dehydrogenation results in increased energy requirements. Since the dehydrogenation is comparatively small its energy requirements may be covered at least partly by excess energy from other processes. More about that later.

As mentioned previously dehydrogenation is energy intensive. The efficiency of this process is thus strongly dependent on the catalyst system employed. The second catalyst system employed for the dehydrogenation is preferably a solid comprising platinum, tin and aluminum oxide. Further catalytically active materials such as zinc and/or calcium for example may also be present. The $Al_2O_3$ is in particular modified with Zn and/or Ca. Such catalysts are often described as Pt/Zn systems and are disclosed in U.S. Pat. No. 4,152,365, U.S. Pat. No. 4,926,005 and U.S. Pat. No. 5,151,401. The dehydrogenation may be effected in presence thereof in the gas phase at a pressure of $0.8*10^5$ Pa to $1.2*10^5$ Pa and a temperature of 450° C. to 700° C. The dehydrogenation is thus heterogeneously catalyzed which makes a complex and costly removal of the second catalyst system from the dehydrogenation mixture unnecessary. The dehydrogenation is preferably carried out at a relatively low temperature between 450° C. and 530° C., which saves energy. The thus achieved product spectrum is appropriate for the purpose required here. Even in this comparatively cold dehydrogenation the pressures should be between $0.8*10^5$ Pa to $1.2*10^5$ Pa.

Since the catalyst is deactivated over time due to coke deposits it needs to be regenerated or replaced regularly. This is made easier by the fact that at least two reactors, each heated and each filled with the second catalyst system, are provided for the dehydrogenation and the reactors are chargeable with subsidiary fraction individually or simultaneously in parallel and/or serially as desired. In this way it is always possible to shut down one reactor and deinstall/regenerate the dehydrogenation catalyst present therein while the other reactor continues to run. The process may accordingly be run continuously. Regeneration is effected by washing with (preferably hot) air or water vapor to burn off the coke. Regeneration is preferably effected in situ, i.e. without deinstallation from the reactor.

A particularly preferred development of the invention provides that the dehydrogenation is operated in an electrically heated reactor. Electrical heating is to be understood as comprehending both ohmic resistance heating and an inductively heated reactor.

An electrically heated dehydrogenation is unusual because such reactors are typically heated with fuel gas. Electrical heating is possible because the dehydrogenation employed here is comparatively small. Electrical heating has the decisive advantage that it may be operated with excess electrical energy as may be generated from renewable energy sources. The dehydrogenation may thus be deliberately operated when a great deal of electricity is generated from wind or solar power due to the prevailing weather conditions but is not in demand in the grid. In this way the plant may provide deliberate negative control capacity.

The selective hydrogenation serves to render harmless contaminants formed in the dehydrogenation, for example polyunsaturated hydrocarbons such as 1,3-butadiene. The valuable alkenes must not be hydrogenated. The selective hydrogenation is effected in the liquid phase at a pressure of $18*10^5$ Pa to $22*10^5$ Pa and at a temperature of 40° C. to 80° C. The catalyst employed is a fixed bed catalyst which comprises 0.1 to 2% by mass of palladium and a support material (activated carbon or aluminum oxide). The selective hydrogenation is effected in the presence of 0.05 to 10 ppm by mass of carbon monoxide based on the mass of the dehydrogenation mixture. The carbon monoxide serves as a moderator and may originate from the dehydrogenation itself. In this way the alkenes are preserved in the selective hydrogenation.

In contrast to the dehydrogenation the selective hydrogenation is effected in the liquid phase. The dehydrogenation mixture must therefore be liquefied before selective hydrogenation. The liquefaction is effected by compression and cooling. The heat recovered during cooling may be used for preheating the subsidiary fraction before dehydrogenation. This saves energy. It is thermodynamically advantageous to implement the cooling as an intercooling arranged between the compression stages.

Alternatively to the Pt/Sn systems the dehydrogenation may also employ a solid comprising aluminum oxide and chromium oxide. Such so-called chromia/alumina catalysts are disclosed in U.S. Pat. No. 3,665,049 and U.S. Pat. No. 3,778,388. The dehydrogenation is then effected in the gas phase at a pressure of $0.8*10^5$ Pa to $1.2*10^5$ Pa and a temperature of 600° C. to 700° C. The remarks made about the Pt/Sn system apply correspondingly to the chromia/alumina catalysts.

A further catalyst system suitable for the dehydrogenation comprises aluminum oxide and magnesiochromite. One example is disclosed in Finocchio et al. Catalysis Today 28 (1996) 381-389. With this catalyst the dehydrogenation is effected in the gas phase at a pressure of $0.8*10^5$ Pa to $1.2*10^5$ Pa and a temperature of 600° C. to 700° C.

As well as the recited heterogeneous systems the dehydrogenation may also be catalyzed homogeneously. This has the advantage that the dehydrogenation can be effected in the liquid phase which enhances process intensity and renders the liquefaction before selective hydrogenation unnecessary. The second catalyst system is then an organometallic compound dissolved in the dehydrogenation reaction mixture.

The organometallic compound may comprise iridium as the central atom to which at least one pincer ligand is complexed. The dehydrogenation would then be effected at a temperature of 100° C. to 250° C. and at a pressure of $800*10^5$ Pa to $1200*10^5$ Pa. Such a process is described in WO2014192020A2.

The organometallic compound may alternatively be [Rh(PMe3)2(CO)Cl]2. This is a photocatalyst which allows dehydrogenation under the action of UV radiation. This is particularly sustainable since sunlight may be used as the energy source:

Chowdhury, A. D., Weding, N., Julis, J., Franke, R., Jackstell, R. and Beller, M. (2014), Towards a Practical Development of Light-Driven Acceptorless Alkane Dehydrogenation. Angew. Chem. Int. Ed., 53: 6477-6481. doi:10.1002/anie.201402287

According to the invention the dehydrogenation is in principle effected without addition of an oxidant such as oxygen. It is not, therefore, an oxidative dehydrogenation (ODH).

Nevertheless, it may be advantageous to add a small amount of oxygen into the dehydrogenation as this allows coke deposits to be removed from the catalyst during normal operation. The heat thus formed is to the benefit of the endothermic dehydrogenation.

In this connection a "small amount of oxygen" is to be understood as meaning an oxygen amount from 1.4 wt % to 14 wt % based on the mass of n-butane present in the subsidiary fraction. This oxygen addition is markedly lower than in a conventional ODH.

In a preferred embodiment of the invention the hydrogenation mixture is mixed with the feedstock mixture as a recyclate without purification. This saves on capital expenditure but presupposes that the selective hydrogenation neutralizes all byproducts of the dehydrogenation that are disruptive toward the hydroformylation.

Ideally, the hydroformylation mixture is exclusively separated into the primary product fraction and the subsidiary fraction. This is possible when, with the exception of the n-butene, no components having a lower boiling point than n-butene are generated in the dehydrogenation.

However, in practice the dehydrogenation will form $C_1$- to $C_3$-hydrocarbons, for instance methane, ethene and propene. This requires a fractionation of the hydroformylation mixture into a low boiler fraction, the subsidiary fraction and the primary product fraction. The $C_1$- to $C_3$-hydrocarbons will then be found in the low boiler fraction.

Such a setup lends itself to fractionating the hydroformylation mixture into the low boiler fraction, the subsidiary fraction, the primary product fraction and into a secondary product fraction, wherein the secondary product fraction has the following composition which sums to 100 wt %:
propanal: 50 wt % to 70 wt %;
n-butanal: 30 wt % to 50 wt %;
other substances: 0 wt % to 10 wt %.

This is because the ethene and propene formed in the dehydrogenation is converted into the corresponding $C_3$-/$C_4$-aldehydes in the hydroformylation. In addition to the n-pentanal these aldehydes represent further products of value which are recovered as secondary product fraction.

The inherently undesired byproducts of the dehydrogenation (ethene, propene) may thus be utilized profitably. The effectiveness of common hydroformylation of a plurality of substrates is demonstrated in WO2015/132068A1 with further references.

A bonus effect of the formation of $C_3$-/$C_4$-aldehydes is that these bind in an azeotrope and thus discharge from the process any water of reaction formed. A separate water removal is thus rendered unnecessary.

Since in the process according to the invention the dehydrogenation is arranged after the hydroformylation in the downstream direction (i.e. in the direction of the added-value chain) a markedly lower production capacity than a commercially available dehydrogenation is sufficient. For arrangement behind an oxo plant on a current industry-standard scale it is sufficient for the apparatus of the dehydrogenation to be configured for continuous processing of a mass flow of the subsidiary fraction of less than 4 kg/s. This size corresponds in continuous operation (8000 h per year) to a plant capacity of 120 kt/a, approximately a fifth of the size that is customary today. A commercially available dehydrogenation plant cannot thus be used since it would be oversized and uneconomic.

Should the butene unconverted in the hydroformylation bring about excessive coking of the second catalyst system employed in the dehydrogenation, the butane/butene mixture could be hydrogenated before dehydrogenation. In this case the subsidiary fraction would be recovered by distillation with subsequent hydrogenation.

A particular advantage of the process described here is that it can be erected not only on greenfield sites but that it is also possible to add an appropriately small dehydrogenation to an existing oxo plant for $C_4$-hydroformylation to enhance the material efficiency of the plant at low capital cost.

The present invention thus also provides for the use of a plant for dehydrogenation of alkanes comprising at least a heated reactor filled with a second catalyst system for retrofitting an existing plant for producing n-pentanal from feedstock mixtures comprising n-butene and n-butane by hydroformylation where the plant for dehydrogenation is arranged downstream of the plant for hydroformylation, said plant for dehydrogenation is fed with a subsidiary fraction from the hydroformylation and the effluent from the dehydrogenation is recycled into the hydroformylation with or without purification.

Figure 2:
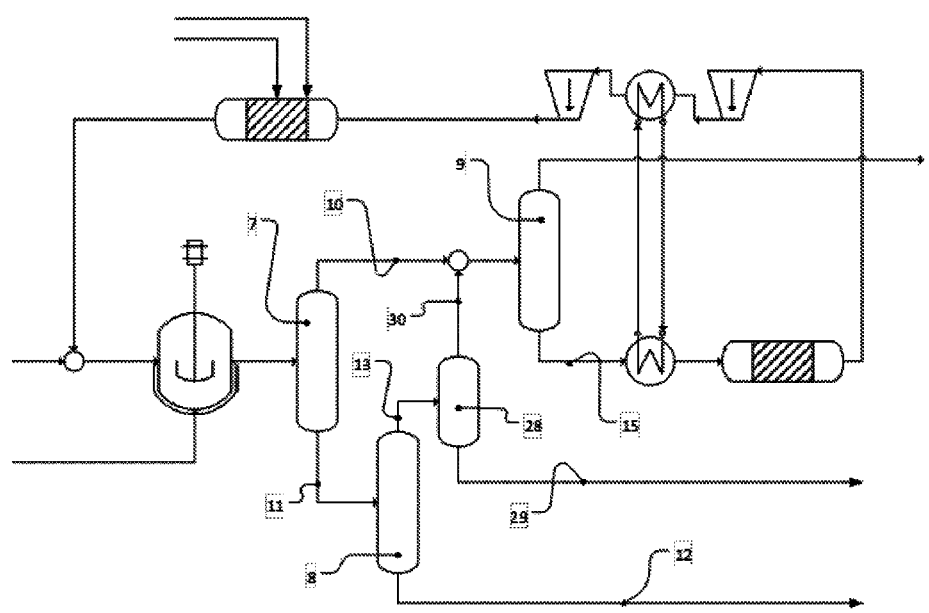
FIG. 2 is a process flow diagram of FIG. 1 additionally showing removal of secondary product.
Figure 3:
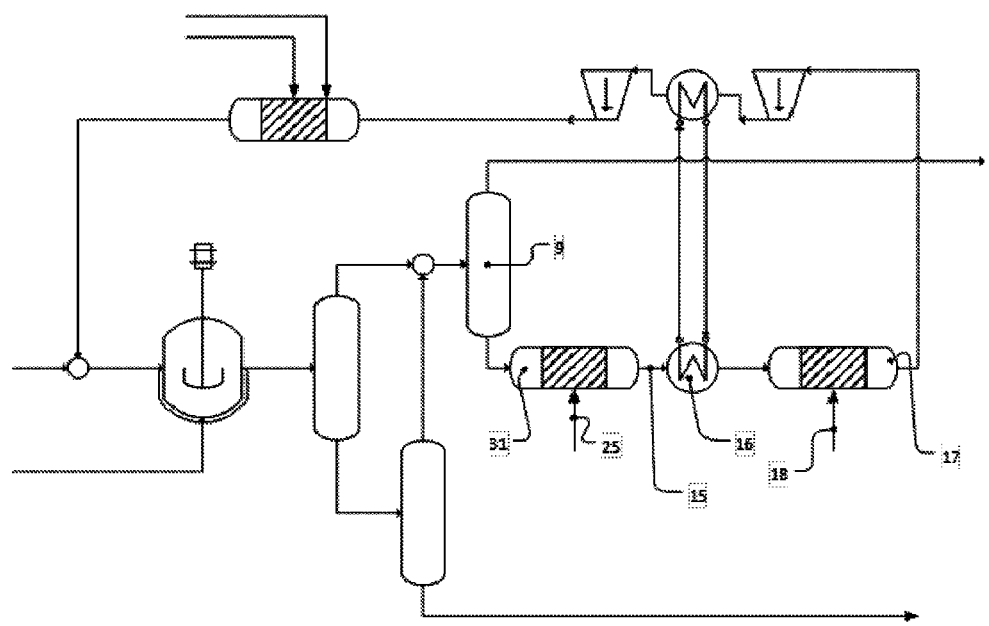
FIG. 3 is a process flow diagram of FIG. 1 additionally showing hydrogenation before dehydrogenation.

The process according to the invention shall now be elucidated with reference to process flow diagrams. In simple terms:

FIG. 1: shows a process flow diagram of the basic concept;

FIG. 2: is as FIG. 1, additionally showing removal of secondary product;

FIG. 3: is as FIG. 1, additionally showing hydrogenation before dehydrogenation.

The basic concept of the process according to the invention is depicted in FIG. 1. A feedstock mixture 1 obtained from outside the process and comprising predominantly n-butane and a residual amount of n-butene is mixed with a recyclate 2 to afford a feed 3. The recyclate originates from the process itself, more about that later.

Feed 3 is run into hydroformylation 4 and there reacted together with synthesis gas 5 (a mixture of carbon monoxide and hydrogen) in customary fashion. Withdrawn from the hydroformylation 4 is a hydroformylation mixture 6 which comprises the desired n-pentanal (formed from the reaction of n-butene with synthesis gas), further byproducts, unconverted n-butene and, especially, unconverted n-butane. The necessary separation of the homogeneous first catalyst system used in the hydroformylation 4 is not depicted here.

In a separation sequence comprising three distillation columns 7, 8, 9 the hydroformylation mixture is fractionated by distillation. To this end the hydroformylation mixture 6 is run into the first column 7 and separated into tops product 10 and bottoms product 11. The bottoms product 11 from the first column 7 is used to feed the second column 8. Obtained at the bottom of the second column is a primary product fraction 12 which comprises the purified n-pentanal.

The tops product 13 from the second column 8 is mixed with the tops product 10 from the first column 7 and run into the third column 9. At the top thereof a low boiler fraction 14 is withdrawn and at the bottom a subsidiary fraction 15.

The subsidiary fraction essentially comprises the non-hydroformylatable n-butane and a significant proportion of n-butene not converted in the hydroformylation 4.

In order to make the carbon atoms present in the subsidiary fraction 15 usable for the process, the subsidiary fraction 15 is initially preheated in a first heat exchanger 16 and then catalytically dehydrogenated in a dehydrogenation 17. The dehydrogenation 17 is effected in the gas phase in the presence of a heterogeneous second catalyst system, optionally with addition of small amounts of oxygen 18.

The dehydrogenation requires thermal energy which is preferably electrically generated. It will be appreciated that traditional heating with fuel gas is also possible.

In the course of the dehydrogenation the n-butane present in the subsidiary fraction 15 is converted into n-butene. Further substances are formed, such as 1,3-butadiene, methane, ethene, propene for instance. The dehydrogenation mixture 19 comprising these substances is withdrawn from the dehydrogenation in gaseous form and then compressed in a first compressor stage 20. The heat from the compressor thus generated is removed by a second heat exchanger 21 and the dehydrogenation mixture 19 is thus intercooled. The heat generated in the intercooling is utilized for preheating the subsidiary fraction 15 before entry into the dehydrogenation 17. To this end the first heat exchanger 16 and the second heat exchanger 21 are interconnected via a circuit 22 which contains a heat transfer medium. The ultimate liquefaction of the dehydrogenation mixture 19 is effected in a second compressor stage 23.

The now liquid dehydrogenation mixture is now subjected to a selective hydrogenation 24 in the presence of a heterogeneous third catalyst system with addition of hydrogen 25 and carbon monoxide 26 as moderator. The selective hydrogenation 24 hydrogenates and thus neutralizes undesired polyunsaturated compounds such as 1,3-butadiene.

The alkenes, by contrast, are preserved.

The hydrogenation mixture 27 withdrawn from the selective hydrogenation 24 is mixed as recyclate 2 with the feedstock mixture 1 and thus ultimately made available to the process again.

The hydrogenation mixture 27 may optionally also be purified and then mixed as recyclate 2 with the feedstock mixture 1. However, this is not preferred and therefore not depicted.

The inventive dehydrogenation and recycling of the recyclate 2 has the effect that the butanes present in the subsidiary fraction 15 reenter the hydroformylation in the form, thanks to the dehydrogenation, of butenes and can there be converted into the primary product n-pentanal. The material efficiency of the process is thus enhanced compared to hydroformylation without dehydrogenation.

As previously mentioned the dehydrogenation 17 produces not only n-butene but also ethene and propene—both hydroformylatable substrates. Provided that the rate of formation of ethene and propene is high enough a fourth column 28 may be provided in the separation sequence, as depicted in FIG. 2. The fourth column 28 is fed with the tops product 13 from the second column 8. A secondary product fraction 29 comprising propanal and n-butanal, both formed from ethene and propene in the hydroformylation 4, may then be withdrawn from the bottom of the fourth column 28. The tops product 30 from the fourth column 28 is mixed with the tops product 10 from the first column 7 and run into the third column 9.

A further alternative embodiment is shown in FIG. 3. Here, the subsidiary fraction 15 is obtained when the bottoms product from the third column 9 is hydrogenated with hydrogen 25 in a hydrogenation 31. This measure is necessary when the content of high-reactivity substances in the bottoms product from the third column 9 would be too high to run said product directly into the dehydrogenation 17. However, such a procedure is not preferred.

LIST OF REFERENCE SYMBOLS

1 Feedstock mixture
2 Recyclate
3 Feed
4 Hydroformylation
5 Synthesis gas
6 Hydroformylation mixture
7 First column
8 Second column
9 Third column
10 Tops product from first column
11 Bottoms product from first column
12 Primary product fraction
13 Tops product from second column
14 Low boiler fraction
15 Subsidiary fraction
16 First heat exchanger
17 Dehydrogenation
18 Oxygen
19 Dehydrogenation mixture
20 First compressor stage
21 Second heat exchanger
22 Circuit
23 Second compressor stage
24 Selective hydrogenation
25 Hydrogen
26 Carbon monoxide
27 Hydrogenation mixture 28 Fourth column
29 Secondary product fraction
30 Tops product from fourth column
31 Hydrogenation

The invention claimed is:

1. A process for producing n-pentanal comprising the steps of:
   a) providing a feedstock mixture having the following composition which sums to 100 wt %:
      n-butane: 70 wt % to 90 wt %;
      n-butene: 10 wt % to 30 wt %;
      1-butene: 0 wt % to 3 wt %;
      isobutene: 0 wt % to 3 wt %;
      isobutane: 0 wt % to 3 wt %;
      1,3-butadiene: 0 wt % to 1 wt %;
      other substances: 0 wt % to 1 wt %;
   b) mixing the feedstock mixture with a recyclate to obtain a feed;
   c) treating the feed with carbon monoxide and hydrogen in the presence of a first catalyst system to convert at least a portion of the n-butene present in the feed into aldehydes by hydroformylation to obtain a hydroformylation mixture;
   d) recovering a primary product fraction from the hydroformylation mixture, wherein the primary product fraction has the following composition which sums to 100 wt %:
      n-pentanal: 90 wt % to 98.5 wt %;
      2-methylbutanal: 0 wt % to 5 wt %;
      3-methylbutanal: 0 wt % to 3 wt %;
      other substances: 0 wt % to 2 wt %;
   e) recovering a subsidiary fraction from the hydroformylation mixture, wherein the subsidiary fraction has the following composition which sums to 100 wt %:
      n-butane: 80 wt % to 92 wt %;
      n-butene: 8 wt % to 20 wt %;
      other substances: 0 wt % to 1 wt %;
   f) subjecting the subsidiary fraction to a dehydrogenation in the presence of a second catalyst system to obtain a dehydrogenation mixture having the following composition which sums to 100 wt %:
      n-butene: 50 wt % to 60 wt %;
      n-butane: 40 wt % to 50 wt %;
      methane: 0 wt % to 4 wt %;
      ethene: 0 wt % to 3 wt %;
      propene: 0 wt % to 2 wt %;
      1,3-butadiene: 0 wt % to 3 wt %;
      other substances: 0 wt % to 1 wt %;
   g) subjecting the dehydrogenation mixture to a selective hydrogenation in the presence of a third catalyst system to obtain a hydrogenation mixture having the following composition which sums to 100 wt %:
      n-butene: 50 wt % to 60 wt %;
      n-butane: 40 wt % to 50 wt %;
      1,3-butadiene: 0 ppm by weight to 500 ppm by weight;
      other substances: 0 wt % to 5 wt %;
   h) direct use of the hydrogenation mixture as recyclate or
      purification of the hydrogenation mixture to obtain the recyclate.

2. The process according to claim 1, wherein the second catalyst system is a solid comprising at least platinum, tin and aluminum oxide and that the dehydrogenation is effected in the gas phase at a pressure of $0.8*10^5$ Pa to $1.2*10^5$ Pa and a temperature of 450° C. to 700° C.

3. The process according to claim 1, wherein at least two reactors, each heated and each filled with the second catalyst system, are provided for the dehydrogenation and the reactors are chargeable with subsidiary fraction individually or simultaneously in parallel and/or serially as desired.

4. The process according to claim 3, wherein the reactors are electrically heated.

5. The process according to claim 1, wherein the dehydrogenation mixture is liquefied by compression and cooling and the selective hydrogenation is effected in the liquid phase at a pressure of $18*10^5$ Pa to $22*10^5$ Pa and a temperature of 40° C. to 80° C.

6. The process according to claim 5, wherein the heat recovered during cooling is used for preheating the subsidiary fraction.

7. The process according to claim 5, wherein the compression is effected in two successive compression stages and that the cooling provided is an intercooling arranged between the compression stages.

8. The process according to claim 1, wherein the second catalyst system is a solid comprising aluminum oxide and chromium oxide and that the dehydrogenation is effected in the gas phase at a pressure of $0.8*10^5$ Pa to $1.2*10^5$ Pa and a temperature of 600° C. to 700° C.

9. The process according to claim 1, wherein the second catalyst system is a solid comprising aluminum oxide and magnesiochromite and that the dehydrogenation is effected in the gas phase at a pressure of $0.8*10^5$ Pa to $1.2*10^5$ Pa and a temperature of 600° C. to 700° C.

10. The process according to claim 1, wherein the dehydrogenation is effected without addition of an oxidant.

11. The process according to claim 1, wherein the dehydrogenation is effected with addition of oxygen, wherein the added amount of oxygen based on the mass of the n-butane present in the subsidiary fraction is 1.4 wt % to 14 wt %.

12. The process according to claim 1, wherein the hydrogenation mixture is mixed with the feedstock mixture as a recyclate without purification.

13. The process according to claim 1, wherein the hydroformylation mixture is exclusively separated into the primary product fraction and the subsidiary fraction.

14. The process according to claim 1, wherein the hydroformylation mixture is separated into a low boiler fraction, the subsidiary fraction and the primary product fraction.

15. The process according to claim 14, wherein the hydroformylation mixture is separated into the low boiler fraction, the subsidiary fraction, the primary product fraction and into a secondary product fraction, wherein the secondary product fraction has the following composition which sums to 100 wt %:
    propanal: 50 wt % to 70 wt %;
    n-butanal: 30 wt % to 50 wt %;
    other substances: 0 wt % to 10 wt %.

16. The process according to claim 1, wherein the mass flow of the subsidiary fraction is less than 4 kg/s and the apparatus of the dehydrogenation is of a size configured for continuous processing of this mass flow.

17. The process according to claim 1, wherein the subsidiary fraction is recovered by distillation with subsequent hydrogenation.

18. A method of a plant for dehydrogenation of alkanes comprising at least a heated reactor filled with a second catalyst system for retrofitting an existing plant for producing n-pentanal from feedstock mixtures comprising the step of hydroformylating of n-butene and n-butane where the plant for dehydrogenation is arranged downstream of the plant for hydroformylation, and feeding said plant for dehydrogenation with a subsidiary fraction from the hydroformylation and the effluent from the dehydrogenation is recycled into the hydroformylation with or without purification.

19. The process according to claim 2, wherein at least two reactors, each heated and each filled with the second catalyst system, are provided for the dehydrogenation and the reactors are chargeable with subsidiary fraction individually or simultaneously in parallel and/or serially as desired.

20. The process according to claim 2, wherein the dehydrogenation mixture is liquefied by compression and cooling and the selective hydrogenation is effected in the liquid phase at a pressure of $18*10^5$ Pa to $22*10^5$ Pa and a temperature of 40° C. to 80° C.

\* \* \* \* \*